United States Patent [19]

Flaugh

[11] Patent Number: 5,654,325
[45] Date of Patent: Aug. 5, 1997

[54] MELATONIN DERIVATIVES FOR USE IN TREATING SLEEP DISORDERS

[75] Inventor: Michael E. Flaugh, Indianapolis, Ind.

[73] Assignee: Eli Lilly and Company, Indianapolis, Ind.

[21] Appl. No.: 154,332

[22] Filed: Nov. 18, 1993

[51] Int. Cl.$^6$ .................. A61K 31/405; A61K 31/40
[52] U.S. Cl. .................................... 514/415; 514/419
[58] Field of Search ........................... 514/415, 419

[56] References Cited

U.S. PATENT DOCUMENTS

| | | | |
|---|---|---|---|
| 4,087,444 | 5/1978 | Flaugh et al. | 260/326.13 B |
| 4,551,471 | 11/1985 | De Luca et al. | 514/419 |
| 4,600,723 | 7/1986 | Short et al. | 514/416 |
| 4,614,807 | 9/1986 | Flaugh | 546/507 |
| 4,665,086 | 5/1987 | Short et al. | 514/416 |
| 4,687,763 | 8/1987 | Wurtmann | 514/53 |
| 4,997,845 | 3/1991 | Flaugh | 514/415 |
| 5,196,435 | 3/1993 | Clemens et al. | 514/284 |
| 5,242,941 | 9/1993 | Lewy et al. | 514/416 |

FOREIGN PATENT DOCUMENTS

| | | | |
|---|---|---|---|
| 513702 A2 | 11/1992 | European Pat. Off. | A61K 31/40 |
| WO89/01472 | 2/1989 | WIPO | C07D 209/14 |

OTHER PUBLICATIONS

Armstrong et. al., *Pharm. Biochem & Beh.*, 46, 45 (1993).
Dahlitz et. al., *The Lancet*, 337, 1121 (1991).
Chu et al., *Endocrinology*, 75, 238 (1964).
Blask et al., *J. Neural. Transm.* [Supp.], 21, 433 (1986).
Blask et al., *Neuroindocrinol Lett.*, 9(2), 63 (1987).
Arendt et al., *Ergonomics*, 30, 1379 (1987).
Waldhauser et al., *Psychopharmacology*, 100, 222 (1990).
Guardiola—Lemaitre, *Adv in Pineal Res.*, 5, 351 (1991).
Lieberman et al., *Brain Res.*, 323, 201 (1984).
Nickelsen et al., *J. Pineal Res.*, 6, 325 (1989).
Arendt et al., *Neuroscience Lett.*, 45, 317 (1984).
Wright et al., *Clin. Endocrinology*, 24, 375 (1986).
*Sleep Disorders:Diagnosis and Treatment*, Chap. 2, John Wiley and Sons (1988).

Primary Examiner—Jerome D. Goldberg
Attorney, Agent, or Firm—Robert D. Titus; Douglas J. Taylor

[57] ABSTRACT

The present invention provides a method of treating sleep disorders using various melatonin analogs.

17 Claims, No Drawings

MELATONIN DERIVATIVES FOR USE IN TREATING SLEEP DISORDERS

BACKGROUND OF THE INVENTION

Melatonin, represented by the structure below:

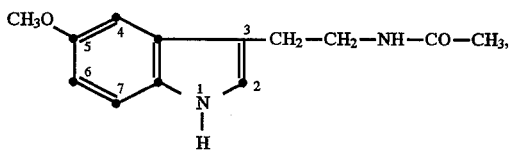

is named systematically as N-[2-(5-methoxy-3-indolyl) ethyl]acetamide. Trivial names for the compound include N-acetyl-5-methoxytryptamine and N-acetyl-O-methylserotonin. Melatonin is a pineal gland hormone which has ovulation inhibitory activity, Chu et al., *Endocrinology*, 75, 238 (1964), as well as some activity against MCF-7 human breast cancer cells, Blask et al. *J. Neural. Transm.* [Supp.], 21, 433 (1986) and for the treatment of mammalian breast carcinoma, Blask et al., *Neuroendocrinol. Lett.*, 9(2), 63 (1987). Furthermore, melatonin has been known to expedite recovery from "jet lag syndrome", Arendt et al., *Ergonomics*, 30, 1379 (1987), to cause sleep, Waldhauser et al., *Psychopharmacology*, 100, 222 (1990) and to minimize disturbances in circadian rhythms of bodily performance and function, U.S. Pat. Nos. 4,600,723 and 5,242,941.

Several melatonin analogues of the formula

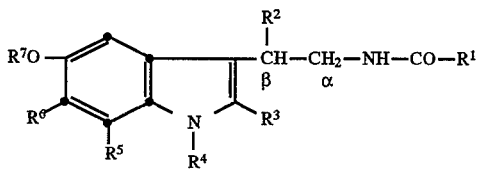

wherein $R^1$ is hydrogen, $C_1$-$C_4$ alkyl or $C_1$-$C_4$ alkoxy;

$R^2$ is hydrogen or $C_1$-$C_4$ alkyl;

$R^3$ is hydrogen or methyl;

$R^4$ is hydrogen, haloacetyl, $C_1$-$C_5$ alkanoyl, benzoyl or benzoyl substituted with halo or methyl;

$R^5$ and $R^6$ are individually hydrogen or halo; and $R^7$ is hydrogen or $C_1$-$C_4$ alkyl;

provided that when $R^2$ is hydrogen, at least one of $R^5$ and $R^6$ is halo, have also been prepared and shown to possess ovulation inhibition activity (see U.S. Pat. Nos. 4997,845 and 4,614,807). Such analogues are also stated to be active in treating hormonally dependent breast carcinomas in U.S. Pat. No. 5,196,435. However, none of these references discloses the utility of such analogs in treating sleep disorders.

Finally, European Patent Application 513,702 discloses that melatonin and its analogues of the formula

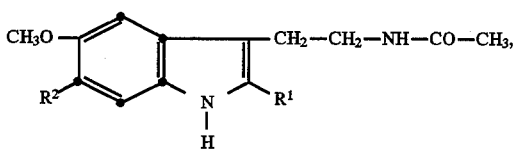

wherein $R^1$ and $R^2$ are the same or different and are hydrogen or halogen can be used in treating sleep disorders and in preanesthetic medication. Again, such disclosure does not teach the instantly claimed method of treating sleep disorders.

It is an object of this invention to provide a method for treating sleep disorders by employing certain melatonin analogs. The instant method is believed to provide a more efficacious (in terms of bioavailability, activity, side effect profile and duration of action) means for treating such disorders than previously known. Further, the melatonin analogues used in the instant method are believed to be completely devoid of toxicity at the dosages required for treatment and, as such, a further object of the present invention is to provide a safe, efficacious, method of treating sleep disorders. Other objects, features and advantages of the present invention will become apparent from the subsequent description and the appended claims.

SUMMARY OF THE INVENTION

This invention provides a method of treating sleep disorders in a mammal suffering from such disorders which comprises administering to said mammal an effective amount of a compound of Formula (I)

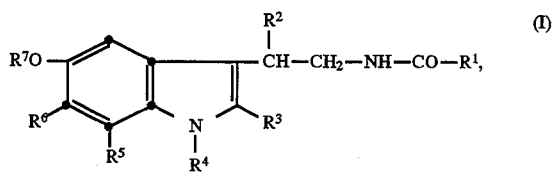

wherein $R^1$ is hydrogen, $C_1$-$C_4$ alkyl or $C_1$-$C_4$ alkoxy;

$R^2$ is hydrogen or $C_1$-$C_4$ alkyl;

$R^3$ is hydrogen, $C_1$-$C_4$ alkyl, phenyl or substituted phenyl;

$R^4$ is hydrogen, haloacetyl, $C_1$-$C_5$ alkanoyl, benzoyl or benzoyl substituted with halo or methyl;

$R^5$ and $R^6$ are each individually hydrogen or halo; and $R^7$ is hydrogen or $C_1$-$C_4$ alkyl;

provided that when $R^3$, $R^4$ and $R^5$ are each hydrogen then $R^2$ must be $C_1$-$C_4$ alkyl.

DETAILED DESCRIPTION OF THE INVENTION

The following definitions refer to the various terms used above and throughout the disclosure.

The term "halo" refers to fluoro, chloro, bromo and iodo.

The term "$C_1$-$C_4$ alkyl" refers to the straight and branched aliphatic radicals of 1–4 carbon atoms including methyl, ethyl, propyl, isopropyl, n-butyl, isobutyl, sec-butyl and tert-butyl.

The term "$C_1$-$C_4$ alkoxy" includes the straight and branched aliphatic ether radicals of 1–4 carbon atoms such as methoxy, ethoxy, propoxy, isopropoxy, n-butoxy, isobutoxy, sec-butoxy and tert-butoxy.

The term "halocetyl" refers to chloroacetyl, bromoacetyl, fluoroacetyl and iodoacetyl.

The term "$C_1$-$C_5$" alkanoyl" includes formyl, acetyl, propionyl, butyryl, α-methylpropionyl, valeryl, α-methylbutyryl, β-methylbutyryl and pivaloyl.

The term "benzoyl substituted with halo" defines mono- and di-halo benzoyl groups. Specific mono-halo benzoyl groups are chlorobenzoyl, bromobenzoyl, fluorobenzoyl and iodobenzoyl.

Di-halo benzoyl groups include those in which both halo substituents are the same. Typical di-halo benzoyl groups include 2,4-dichlorobenzoyl, 2,4-dibromobenzoyl, 2,4-diflluorobenzoyl and 2,4-diiodobenzoyl.

The term "benzoyl substituted with methyl" contemplates methylbenzoyl, dimethylbenzoyl and trimethylbenzoyl.

The term "substituted phenyl" refers to a phenyl ring which is substituted with one or two substituents selected from the group consisting of halo, $C_1$–$C_4$ alkyl or $C_1$–$C_4$ alkoxy. Examples of such term, therefore, include 4-chlorophenyl, 2-fluorophenyl, 3-iodophenyl, 4-bromophenyl, 3,4-dibromophenyl, 4-methylphenyl, 2-ethylphenyl, 3-n-propylphenyl, 4-isopropylphenyl, 4-n-butylphenyl, 3-t-butylphenyl, 4-sec-butylphenyl, 3,4-dimethylphenyl, 4-methoxyphenyl, 3-ethoxyphenyl, 2-n-propylphenyl, 4-isopropoxyphenyl, 3-isobutoxyphenyl, 4-t-butoxyphenyl, 3-ethoxy-4-methoxyphenyl and the like.

While all of the compounds of Formula I are believed to be useful for the method of treating sleep disorders presented herein, certain of such compounds are preferred for such use. Preferred compounds of Formula I for use in the instantly claimed method include those compounds wherein $R^1$ is $C_1$–$C_4$ alkyl (especially methyl), $R^3$ is hydrogen or $C_1$–$C_4$ alkyl (especially methyl) and $R^4$ is hydrogen.

Of such preferred compounds, particularly preferred compounds include those wherein $R^2$ and $R^7$ are each independently $C_1$–$C_4$ alkyl (preferably methyl). The most preferred compounds for use in the method of the present invention include N-[2-methyl-2-(5-methoxy-6-fluoroindol-3-yl) ethyl]acetamide, N-[2-ethyl-2-(5-methoxy-6-chloroindol-3-yl)ethyl]acetamide, N-[2-methyl-2-(5-methoxy-6,7-dichloroindol-3-yl)ethyl]acetamide and N-[2-methyl-2-(5-methoxy-6-chloroindol-3-yl)ethyl]acetamide. The later compound is especially preferred for purposes of the present invention.

Those compounds employed in the method of the present invention wherein $R^2$ is $C_1$–$C_4$ alkyl have an asymmetric center at the carbon atom to which such $R^2$ substituent is attached (i.e., the β-carbon atom). As such, such $R^2$ substituted compounds can exist as either a racemic mixture or as individual stereoisomers. All such types of compounds are contemplated for use in the method of the present invention.

The following list illustrates representative compounds suitable for use in the present invention.

N-[2-methyl-2-(5-methoxy-6-chloroindol-3-yl)ethyl] acetamide

N-[2-methyl-2-(5-methoxy-6-fluoroindol-3-yl)ethyl] acetamide

N-[2-ethyl-2-(5-methoxy-6-fluoroindol-3-yl)ethyl] acetamide

N-[2-ethyl-2-(5-methoxy-6-chloroindol-3-yl)ethyl] acetamide

N-[2-isopropyl-2-(5-methoxy-6-chloroindol-3-yl)ethyl] acetamide

N-[2-isoprophyl-2-(5-methoxy-6-fluoroindol-3-yl)ethyl] acetamide

N-[2-methyl-2-(5-methoxy-6-bromoindol-3-yl)ethyl] formamide

N-[2-butyl-2-(5-methoxy-6-bromoindol-3-yl)ethyl] formaide

N-[2-ethyl-2-(5-propoxy-6-chloroindol -3-yl)ethyl] formamide

N-[2-propyl-2-(5-isopropoxy-6-iodoindol-3-yl)ethyl] formamide

N-[2-methyl-2-(5-methoxy-6-chloroindol-3-yl)ethyl] propionamide

N-[2-ethyl-2-(5-methoxy-6-fluoroindol-3-yl)ethyl] propionamide

N-[2-methyl-2-(5-ethoxy-6-bromoindol-3-yl)ethyl] propionamide

N-[2-methyl-2-(5-ethoxy-6-fluoroindol-3-yl)ethyl] butyramide

N-[2-propyl-2-(5-butoxy-6-chloroindol-3-yl)ethyl] butyramide

N-[2-methyl-2-(5-methoxy-6-chloroindol-3-yl)ethyl] butyramide

N-[2-methyl-2-5-methoxy-7-chloroindol-3-yl)ethyl] acetamide

N-[2-methyl-2-5-methoxy-7-fluoroindol-3-yl)ethyl] acetamide

N-[2-ethyl-2-(5-methoxy-7-chloroindol-3-yl)ethyl] acetamide

N-[2-propyl -2-(5-methoxy-7-bromoindol-3-yl)ethyl] acetamide

N-[2-ethyl -2-(5-t-butoxy-7-chloroindol-3-yl)ethyl] formamide

N-[2-ethyl-2-(5-ethoxy-7-iodoindol-3-yl)ethyl]formamide

N-[2-methyl-2-(5-isopropoxy-7-chloroindol-3-yl)ethyl] formamide

N-[2-methyl-2-(5-methoxy-7-bromoindol-3-yl)ethyl] propionamide

N-[2-ethyl -2-(5-propoxy-7-chloroindol-3-yl)ethyl] propionamide

N-[2-methyl-2-(5-s-butoxy-7-fluoroindol-3-yl)ethyl] propionamide

N-[2-methyl-2-(5-methoxy-7-chloroindol-3-yl)ethyl] butyramide

N-[2-butyl-2-(5-ethoxy-7-chloroindol-3-yl)ethyl] butyramide

N-[2-ethyl-2-(5-methoxy-7-fluoroindol-3-yl)ethyl] butyramide

N-[2-methyl-2-(5-methoxy-6,7-dichloroindol-3-yl)ethyl] acetamide

N-[2-ethyl -2-(5-methoxy-6,7-dichloroindol-3-yl)ethyl] acetamide

N-[2-isopropyl-2-(5-methoxy-6,7-dichloroindol-3-yl)ethyl] acetamide

N-[2-methyl-2-(5-isopropoxy-6,7-dichloroindol-3-yl)ethyl] acetamide

N-[2-methyl-2-(5-methoxy-6,7-difluoroindol-3-yl)ethyl] acetamide

N-[2-propyl-2-(5-methoxy-6,7-difluoroindol-3-yl)ethyl] acetamide

N-[2-ethyl-2-(5-butoxy-6,7-difluoroindol-3-yl)ethyl] acetamide

N-[2-methyl-2-(5-methoxy-6-chloro-7-fluoroindol-3-yl) ethyl]acetamide

N-[2-methyl-2-(5-methoxy-6-chloro-7-bromoindol-3-yl) ethyl]acetamide

N-[2-methyl-2-(5-methoxy-6-fluoro-7-chloroindol-3-yl) ethyl]acetamide

N-[2-methyl -2-(5-ethoxy-6-bromo-7-iodoindol-3-yl)ethyl] acetamide

N-[2-ethyl-2-(5-ethoxy-6-chloro-7-fluoroindol-3-yl)ethyl] acetamide

N-[2-isopropyl-2-(5-t-butoxy-6-chloro-7-fluoro-indol-3-yl) ethyl]acetamide

N-[2-ethyl-2-(5-butoxy-6-bromo-7-chloroindol-3-yl)ethyl] acetamide

N-[2-methyl-2-(5-methoxy-6,7-dichloroindol-3-yl)ethyl] formamide

N-[2-methyl-2-(5-methoxy-6,7-dibromoindol-3-yl)ethyl] formamide

N-[2-t-butyl-2-(5-methoxy-6-chloro-7-fluoroindol-3-yl) ethyl]formamide
N-[2-ethyl-2-(5-ethoxy-6-fluoro-7-bromoindol-3-yl)ethyl] formamide
N-[2-ethyl-2-(5-s-butoxy-6-fluoro-7-chloroindol-3-yl) ethyl]formamide
N-[2-methyl-2-(5-methoxy-6,7-dichloroindol-3-yl)ethyl] propionamide
N-[2-ethyl-2-(5-methoxy-6,7-dichloroindol-3-yl)ethyl] propionamide
N-[2-propyl-2-(5-isopropoxy-6-chloro-7-fluoroindol-3-yl) ethyl]propionamide
N-[2-methyl-2-(5-methoxy-6-bromo-7-iodoindol-3-yl) ethyl]propionamide
N-[2-methyl-2-5-ethoxy-6-bromo-7-chloroindol-3-yl)ethyl] propionamide
N-[2-methyl -2-5-methoxy-6,7-difluoroindol-3-yl)ethyl] butyramide
N-[2-ethyl-2-(5-methoxy-6-fluoro-7-chloroindol-3-yl) ethyl]butyramide
N-[2-isopropyl-2-(5-methoxy-6,7-dibromoindol-3-yl)ethyl] butyramide
N-[2-isopropyl-2-5-butoxy-6-bromo-7-chloroindol-3-yl) ethyl]butyramide
N-[2-ethyl -2-(5-methoxy-6,7-dichloro-3-yl)ethyl] butyramide
N-[2-methyl-2-(1-acetyl-5-methoxy-6-chloroindol-3-yl) ethyl]acetamide
N-[2-butyl-2-(1-acetyl-5-methoxy-6-fluoroindol-3-yl)ethyl] acetamide
N-[2-ethyl-2-(1-acetyl-5-isopropoxy-6-chloro-7-fluoroindol-3-yl)ethyl]acetamide
N-[2-methyl-2-(1-propionyl-5-methoxy-6-fluoroindol-3-yl) ethyl]acetamide
N-[2-methyl -2-(1-propionyl -5-ethoxy-6,7-dichloroindol -3-yl)ethyl]acetamide
N-[2-ethyl-2-(1-propionyl-5-butoxy-7-chloroindol-3-yl) ethyl]acetamide
N-[2-methyl -2-(1-pivaloyl -5-ethoxy-6-bromoindol-3-yl) ethyl]formamide
N-[2-propyl-2-(1-chloroacetyl-5-methoxy-6-bromo-7-fluoroindol-3-yl)ethyl]propionamide
N-[2-methyl-2-(1-bromoacetyl -5-ethoxy -7-chloro-indol-3-yl)ethyl]butyramide
N-[2-ethyl-2-(1-valeryl -5-isopropoxy-6,7-dichloroindol-3-yl)ethyl]acetamide
N-[2-methyl-2-(1-butyryl-5-methoxy-6-chloroindol-3-yl) ethyl]acetamide
N-[2-ethyl-2-(1-benzoyl-5-t-butoxy-7-bromoindol-3-yl) ethyl]formamide
N-[[2-isopropyl-2-[1-(4-chlorobenzoyl)-5-methoxy-7-fluoroindol-3-yl]ethyl]]formamide
N-[[2-methyl-2-[1-(4-bromobenzoyl)-5-ethoxy-6,7-dichloroindol-3-yl]ethyl]]propionamide
N-[[2-ethyl-2-[1-(2,4-dichlorobenzoyl)-5-methoxy-7-bromoindol-3-yl]ethyl]]propionamide
N-[[2-methyl-2-[1-(2,4-difluorobenzoyl)-5-propoxy-6-chloroindol-3-yl]ethyl]]formamide
N-[[2-methyl-2-[1-(4-iodobenzoyl)-5-ethoxy-6-fluoro-7-chloroindol-3-yl]ethyl]]acetamide
N-[[2-ethyl-2-[1-(2-methylbenzoyl)-5-methoxyindol-3-yl] ethyl]]propionamide
N-[[2-methyl-2-[1-(4-fluorobenzoyl)-5-ethoxyindol-3-yl] ethyl]]formamide
N-[[2-methyl-2-[1-(2,6-dimethylbenzoyl)-5-methoxy-7-fluoroindol-3-yl]ethyl]]formamide
N-[[2-ethyl-2-[1-(2,6-dimethylbenzoyl)-5-ethoxyindol-3-yl]ethyl]]acetamide
N-[[2-ethyl-2-[1-(2,4,6-trimethoxybenzoyl)-5-methoxy-6-chloroindol-3-yl]ethyl]]propionamide
N-[[2-methyl-2-[1-(2,4,6-trimethoxybenzoyl)-5-methoxyindol-3-yl]ethyl]]formamide
N-[2-ethyl-2-(1-pivaloyl-5-isopropoxyindol-3-yl)ethyl] acetamide
N-[2-methyl-2-(1-chloroacetyl -5-methoxyindol-3-yl)ethyl] butyramide
N-[2-methyl-2-(5-methoxyindol-3-yl)ethyl]acetamide
N-[2-ethyl-2-(5-methoxyindol-3-yl)ethyl]acetamide
N-[2-ethyl-2-(5-methoxyindol -3-yl)ethyl]propionamide
N-[2-methyl-2-(5-propoxyindol-3-yl)ethyl]formamide
N-[2-methyl-2-(5-s-butoxyindol-3-yl)ethyl]butyramide
N-[2-ethyl-2-(5-ethoxyindol-3-yl)ethyl]propionamide
N-[2-methyl-2-(5-ethoxyindol -3-yl)ethyl]formamide
N-[2-isopropyl-2-(5-methoxyindol-3-yl)ethyl]acetamide
N-[2-ethyl-2-(5-methoxyindol-3-yl)ethyl]formamide
N-[2-(2-methyl-5-methoxy-6-bromoindol-3-yl)ethyl] acetamide
N-[2-(2-ethyl-5-methoxy-6-chloroindol-3-yl)ethyl] acetamide
N-[2-(2-n-propyl-5-methoxy-6-chloroindol-3-yl)ethyl] formamide
N-[2-(2-n-butyl-5-methoxy-6-chloroindol-3-yl)ethyl] formamide
N-[2-(2-ethyl-5-methoxy-6-iodoindol-3-yl)ethyl] propionamide
N-[2-(2-isopropyl-5-methoxy-6-fluoroindol-3-yl)ethyl]α-methylpropionamide
N-[2-(2-phenyl-5-methoxy-6-chloroindol-3-yl)ethyl] formamide
N-[2-(2-phenyl-5-methoxy-6-bromoindol-3-yl)ethyl] acetamide
N-[2-(2-phenyl-5-methoxy-6-iodoindol-3-yl)ethyl] propionamide
N-[2-((2-(4-chlorophenyl)-5-methoxy-6-chloroindol-3-yl)) ethyl]formamide
N-[2-((2-(3-fluorophenyl)-5-methoxy-6-bromoindol-3-yl)) ethyl]acetamide
N-[2-((2-(2-fluorophenyl)-5-methoxy-6-chloroindol-3-yl)) ethyl]propionamide
N-[2-((2-(4-methylphenyl)-5-methoxy-6-bromoindol-3-yl)) ethyl]formamide
N-[2-((2-(3-ethylphenyl)-5-methoxy-6-fluoroindol-3-yl)) ethyl]butyramide
N-[2-((2-(4-n-propylphenyl)-5-methoxy-6-chloroindol-3-yl))ethyl]formamide
N-[2-((2-(3-isopropylphenyl)-5-methoxy-6-fluoroindol-3-yl))ethyl]acetamide
N-[2-((2-(4-methoxyphenyl)-5-methoxy-6-chloroindol-3-yl))ethyl]propionamide
N-[2-((2-(3-ethoxyphenyl)-5-methoxy-6-bromoindol-3-yl)) ethyl]acetamide
N-[2-((2-(3-n-propoxyphenyl)-5-methoxy-6-fluoroindol-3-yl))ethyl]acetamide
N-[2-((2-(4-t-butoxyphenyl)-5-methoxy-6-chloroindol-3-yl))ethyl]formamide
N-[2-((2-(3-n-butoxyphenyl)-5-methoxy-6-chloroindol-3-yl))ethyl]acetamide
N-[2-(1-acetyl-5-methoxy-6-chloroindol-3-yl)ethyl] acetamide
N-[2-(1-propionyl-5-methoxy-6-fluoroindol-3-yl)ethyl] acetamide
N-[2-(1-pivaloyl-5-methoxy-6-bromoindol-3-yl)ethyl] formamide
N-[2-(1-chloroacetyl-5-methoxy-6-iodoindol-3-yl)ethyl] propionamide N-[2-(1-bromoacetyl-5-methoxy-6-chloroindol-3-yl)ethyl]-n-butyramide N-[2-(1-valeryl-2-methyl-5-methoxy-6-bromoindol-3-yl)ethyl]acetamide N-[2-(1-butyryl-2-ethyl-5-methoxy-6-chloroindol-3-yl)ethyl]acetamide N-[2-(1-benzoyl-2-n-propyl-5-methoxy-6-chloroindol-3-yl)ethyl]formamide N-[[2-[1-(4-chlorobenzoyl)-2-n-butyl-5-methoxy-6-chloroindol-3-yl]ethyl]]formamide N-[[2-[1-(4-bromobenzoyl)-2-ethyl-5-methoxy-6-iodoindol-3-yl]ethyl]]propionamide N-[[2-[1-(2,4-dichlorobenzoyl)-2-isopropyl-5-methoxy-6-fluoroindol-3-yl]ethyl]]-α-methylpropionamide N-[[2-[1-(2,4-difluorobenzoyl)-2-phenyl-5-methoxy-6-chloroindol-3-yl]ethyl]]formaide N-[[2-[1-(4-iodobenzoyl)-2-phenyl-5-methoxy-6-bromoindol-3-yl]ethyl]]acetamide N-[[2-[1-(2-methylbenzoyl)-2-phenyl-5-methoxy-6-iodoindol-3-yl]ethyl]]propionamide N-[[2-[1-(2,6-dimethylbenzoyl)-2-(4-chloro-phenyl)-5-methoxy-6-chloroindol-3-yl]ethyl]]formamide N-[[2-[1-(2,4,6-trimethylbenzoyl)-2-(3-fluoro-phenyl)-5-methoxy-6-bromoindol-3-yl]ethyl]]acetamide N-[2-(1-pivaloyl-5-methoxy-6-chloroindol-3-yl)ethyl]acetamide N-[2-(1-chloroacetyl-5-methoxy-6-chloroindol -3-yl)ethyl]acetamide N-[[2-[1-(4-chlorobenzoyl)-5-methoxy-6-chloroindol-3-yl]ethyl]]acetamide N-[[2-[1-(2,4-dichlorobenzoyl)-5-methoxy-6-chloroindol-3-yl]ethyl]]acetamide N-[[2-[1-(2-methylbenzoyl)-5-methoxy-6-chloroindol-3-yl]ethyl]]acetamide N-[[2-[1-(2,6-dimethylbenzoyl)-5-methoxy-6-chloroindol-3-yl]ethyl]]acetamide N-[[2-[1-(2,4,6-trimethylbenzoyl)-5-methoxy-6-chloroindol-3-yl]ethyl]]acetamide N-[2-(5-methoxy-6,7-dichloroindol-3-yl)ethyl]acetamide N-[2-(2-methyl-5-methoxy-6,7-difluoroindol-3-yl)ethyl]acetamide N-[2-(2-methyl-5-methoxy-6-fluoro-7-chloroindol-3-yl)ethyl]acetamide N-[2-(5-methoxy-6,7-dichloroindol-3-yl)ethyl]propionamide N-[2-(5-methoxy-6,7-difluoroindol-3-yl)ethyl]isobutyramide N-[2-(2-methyl-5-methoxy-6,7-dichloroindol-3-yl)ethyl]-n-butyramide; and the like.

The compounds employed in the method of this invention are known in the art or can be made by methods described in the art. Representative publications which teach the preparation of compounds of Formula I include U.S. Pat. Nos. 4,087,444; 4,614,807; and 4,997,845. The teaching of all such patents is hereby incorporated by reference.

The compounds of Formula I, as used in this invention, are useful in treating sleep disorders in mammals. Such disorders, as defined for purposes of the present invention, are characterized by difficulty in initiating or maintaining sleep (DIMS disorders) or in obtaining restful sleep. As such, the sleep disorders encompassed by the present invention include insomnia, those instances where the patient is only able to obtain a minimal period of sleep or where the patient is only able to obtain a poor quality sleep in terms of patient restfulness. A discussion of sleep disorders, the different stages of sleep and some of the effects coming from lack of same are reported in Goodman and Gillman, The *Pharmacological Basis of Therapeutics*, 360 (1982), Williams et al., *Sleep Disorders: Diagnosis and Treatment*, John Wiley and Sons, Chapter 2 (1988) and European Patent Application 513,702. The teachings of such references with respect to the scope, extent and cause of sleep disorders is herein incorporated by reference.

As discussed above, the compounds of Formula I are useful in treating sleep disorders in mammals. Such method comprises administering to a mammal (preferably a human) in need of such treatment a sufficient amount of one or more compounds of Formula I so as to achieve the therapeutic intervention desired. The compounds can be administered by a variety of routes including the oral, rectal, transdermal, subcutaneous, intravenous, intramuscular or intranasal routes. The oral and transdermal routes are preferred. No matter what route of administration is chosen, such administration is accomplished by means of pharmaceutical compositions which are prepared by techniques well known in the pharmaceutical sciences.

As mentioned above, the method of the present invention utilizes pharmaceutical compositions. In making these compositions, one or more active ingredients will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated so as to provide rapid, sustained or delayed release of the active ingredient after administration to the patient by employing procedures well known in the art.

The compositions are formulated, preferably in a unit dosage form, such that each dosage contains from about 1 to about 500 mg, more usually about 30 to about 200 mg, of the active ingredient. The term "unit dosage form" refers to physically discrete units suitable as unitary dosages for human subjects and other mammals, each unit containing a predetermined quantity of active material calculated to produce the desired therapeutic effect, in association with one or more suitable pharmaceutical diluents, excipients or carriers.

The compounds employed in the method of the present invention are effective over a dosage range of about 1 mg of active ingredient per day to about 500 mg of active ingredient per day for treating sleep disorders. Thus, as used herein, the term "effective amount" refers to a dosage range of from about 1 to about 500 mg of active ingredient per day. In the treatment of adult humans, the range of about 30 to about 200 mg of active ingredient per day, in single or divided doses, is preferred. However, it will be understood that the amount of compound actually administered will be determined by a physician, in light of the relevant circumstances including the choice of compound to be administered, the chosen route of administration, the age, weight, and response of the individual patient, and the severity of the patient's sleep disorder symptoms.

The following formulation examples may employ as active ingredient any of the compounds of Formula I. The examples are illustrative only and are not intended to limit the scope of the invention in any way.

EXAMPLE 1

Hard gelatin capsules suitable for treating a sleep disorder are prepared using the following ingredients:

|  | Quantity (mg/capsule) |
|---|---|
| (±)-N-[2-methyl-2-(5-methoxy)-6-chloroindol-3-yl)ethyl]acetamide | 50 |
| Starch dried | 200 |
| Magnesium stearate | 10 |

The above ingredients are mixed and filled into hard gelatin capsules in 260 mg quantities.

EXAMPLE 2

A tablet suitable for treating sleep disorders is prepared using the ingredients below:

|  | Quantity (mg/tablet) |
|---|---|
| (−)-N-[2-methyl-2-(5-methoxy)-6-chloroindol-3-yl)ethyl]acetamide | 100 |
| Cellulose, microcrystalline | 400 |
| Silicon dioxide | 10 |
| Stearic acid | 5 |

The components are blended and compressed to form tablets each weighing 515 mg.

EXAMPLE 3

An aerosol solution suitable for treating sleep disorders is prepared containing the following components:

|  | Weight |
|---|---|
| (±)-N-[2-methyl-2-(5-methoxy-6-fluoroindol-3-yl)ethyl]acetamide | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. Valve units are then fitted to the container.

EXAMPLE 4

Tablets suitable for a sleep disorder, each containing 60 mg of active ingredient are made up as follows:

| | |
|---|---|
| (+)-N-[2-methyl-2-(5-methoxy)-6-chloroindol-3-yl)ethyl]acetamide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 5

Capsules suitable for treating sleep disorders, each containing 80 mg of medicament, are made as follows:

| | |
|---|---|
| (−)-N-[2-methyl-2-(5-methoxy)-6,7-dichloroindol-3-yl)ethyl]acetamide | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 6

Suppositories suitable for treating sleep disorders, each containing 100 mg of active ingredient, are made as follows:

| | |
|---|---|
| (±)-N-[2-ethyl-2-(5-methoxy-6-chloroindol-3-yl)ethyl]acetamide | 100 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 7

Suspensions suitable for treating sleep disorders, each containing 50 mg of medicament per 5 ml dose, are made as follows:

| | |
|---|---|
| (±)-N-[2-methyl-2-(5-methoxy-6-chloroindol-3-yl)ethyl]acetamide | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 8

Capsules suitable for use in treating a sleep disorder, each containing 100 mg of medicament, are made as follows:

| | |
|---|---|
| (±)-N-[2-methyl-2-(5-methoxy-6,7-dichloroindol-3-yl)ethyl]acetamide | 100 mg |
| Starch | 164 mg |
| Microcrystalline cellulose | 164 mg |
| Magnesium stearate | 22 mg |
| Total | 450 mg |

The active ingredient, cellulose, starch and magnesium stearate are blended, passed through a No. 45 mesh U.S. sieve, and filled into hard gelatin capsules in 450 mg quantities.

I claim:

1. A method of treating sleep disorders in a mammal suffering from such disorders which comprises administering to said mammal an effective amount of a compound of the formula

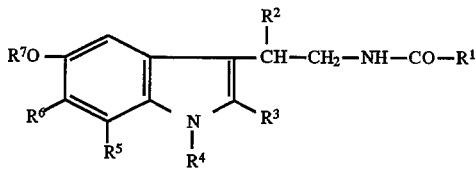

wherein $R^1$ is hydrogen, $C_1$–$C_4$ alkyl or $C_1$–$C_4$ alkoxy;

$R^2$ is hydrogen or $C_1$–$C_4$ alkyl;

$R^3$ is hydrogen, $C_1$–$C_4$ alkyl, phenyl or substituted phenyl;

$R^4$ is hydrogen, haloacetyl, $C_1$–$C_5$ alkanoyl, benzoyl or benzoyl substituted with halo or methyl $R^5$ and $R^6$ are each independently hydrogen or halo; and $R^7$ is hydrogen or $C_1$–$C_4$ alkyl; provided that when $R^3$, $R^4$ and $R^5$ are each hydrogen then $R^2$ must be $C_1$–$C_4$ alkyl.

2. A method of claim 1 which employs a compound wherein $R^4$ is hydrogen.

3. A method of claim 2 which employs a compound wherein $R^1$ is $C_1$–$C_4$ alkyl.

4. A method of claim 3 which employs a compound wherein $R^3$ is hydrogen or $C_1$–$C_4$ alkyl.

5. A method of claim 4 which employs a compound wherein $R^1$ is methyl and $R^3$ is hydrogen.

6. A method of claim 4 which employs a compound wherein both $R^1$ and $R^3$ are methyl.

7. A method of claim 4 which employs a compound wherein $R^7$ is $C_1$–$C_4$ alkyl.

8. A method of claim 7 which employs a compound wherein $R^2$ is $C_1$–$C_4$ alkyl.

9. A method of claim 8 which employs a compound wherein $R^7$ is methyl.

10. A method of claim 9 which employs a compound wherein $R^2$ is methyl.

11. A method of claim 10 which employs N-[2-methyl-2-(5-methoxy-6-fluoroindol-3-yl)ethyl]acetamide.

12. A method of claim 9 which employs N-[2-ethyl-2-(5-methoxy-6-chloroindol-3-yl)ethyl]acetamide.

13. A method of claim 10 which employs N-[2-methyl-2-(5-methoxy-6,7-dichloroindol-3-yl)ethyl]acetamide.

14. A method of claim 10 which employs N-[2-methyl-2-(5-methoxy-6-chloroindol-3-yl)ethyl]acetamide.

15. A method of claim 14 which employs the racemate of the compound described therein.

16. A method of claim 14 which employs the (−) stereoisomer of the compound described therein.

17. A method of claim 14 which employs the (+) stereoisomer of the compound described therein.

* * * * *